United States Patent [19]
Pesenti et al.

[11] Patent Number: 5,460,171
[45] Date of Patent: Oct. 24, 1995

[54] SYNCHRONIZATION DEVICE FOR AEROSOL APPLIANCES WITH PRESSURIZED REGULATING BOTTLE

[76] Inventors: Yvan Pesenti, 3, rue Thiers, 38000 Grenoble; Jean-Philippe Quenderff, 40, chemin de la Revirée, 38240 Meylan, both of France

[21] Appl. No.: 244,097
[22] PCT Filed: Nov. 13, 1992
[86] PCT No.: PCT/EP92/02615
  § 371 Date: May 16, 1994
  § 102(e) Date: May 16, 1994
[87] PCT Pub. No.: WO93/09830
  PCT Pub. Date: May 27, 1993
[30] Foreign Application Priority Data
  Nov. 15, 1991 [FR] France ................................ 91 14367
[51] Int. Cl.⁶ ................................................ A61M 11/00
[52] U.S. Cl. .......................... 128/200.23; 128/203.12; 128/200.14
[58] Field of Search ................ 128/200.23, 200.14, 128/203.12

[56] References Cited
U.S. PATENT DOCUMENTS
4,852,561  8/1989  Sperry .................. 128/200.23
5,031,610  7/1991  Armstrong et al. ............... 128/200.23

*Primary Examiner*—Edgar S. Burr
*Assistant Examiner*—William J. Deane, Jr.
*Attorney, Agent, or Firm*—Reese Taylor

[57] ABSTRACT

An appliance intended to synchronize inhaling by the user of an aerosol device which sprays a dose of active element released from a regulating bottle includes a closing valve for restricting inhaling by the user through the appliance until the user activates the valve to release a dose of the active element from the bottle and provide for subsequent unimpeded inhalation. The appliance also includes a damper valve to allow the user to exhale through the appliance prior to attempting to inhale with the damper valve being positioned to be opened by the regulating bottle sliding in the appliance. Another form of the invention includes a runner which receives the regulating bottle with the runner serving to activate the regulating bottle to release the dose of the active element therefrom. The valve includes, in one form of the invention, at least one slot in the body of the appliance and one slot in the runner which slots may be brought into registry to allow the user to inhale.

8 Claims, 5 Drawing Sheets

SYNCHRONIZATION DEVICE FOR AEROSOL APPLIANCES WITH PRESSURIZED REGULATING BOTTLE

The invention is used in portable regulating aerosol appliances for pharmaceutical applications.

The appliances are intended for vaporizing and spraying of an active element in the respiratory system of the user.

Generally, the appliances consist of a body equipped with a mouth or nose piece, a regulating bottle containing the product to be sprayed, an injection duct connected to the regulating bottle and opening up into the mouth or nose piece.

To use the appliances, the user must simultaneously press the regulating bottle, while he inhales in the mouth or nose piece, in order to drive the sprayed dose of the product into the respiratory tracts.

Unfortunately, the efficiency of the device greatly depends on the ability of user to correctly synchronize both manoeuvers.

Extensive research has resulted in automatic and semi-automatic appliances whereby the active element is injected by the patient when he inhales in the appliance. Such appliances are frequently based on complex and rather expensive methods which are sometimes quite unreliable.

The device in this invention cures these disadvantages and offers a simple, economical and reliable solution to the synchronization problem.

In the device in this invention, the user is prevented from or very restricted in inhaling, until the manoeuver for releasing the dose of active element has been executed. Therefore, the user has more time available to activate the regulating bottle, as soon as he has started his attempt to inhale through the appliance, without reducing the synchronization action.

Therefore, the device, which is built with the same general design of conventional appliances, that is: regulating bottle, mouth piece, has, in addition thereto, a closing device, acting as a valve, which opens with the motion that activates the release of a dose of the product from the regulating piece.

This valve, which remains closed when the appliance is in neutral position, prevents or restricts the user from inhaling in the appliance until he has activated the regulating piece, which shall then trigger the opening of the valve, followed by an injection of one dose of active element, in synchronization with inhalation by user.

This implies that previously thereto, the user must have exhaled as deeply as possible prior to putting the appliance in his mouth, after which he should have tried to inhale into the appliance prior to the activating of the regulating bottle.

In addition, the device can be equipped with a damper valve which shall allow user to exhale through the appliance.

We can see that this device is less elaborate than automatic appliances, but that it offers some help for synchronizing, by using simple, reliable and inexpensive methods.

Other advantages and features shall appear more clearly from the following statement of the specific execution modes of the invention, given as non-limitative examples and shown on the drawings, where:

Figure 1:
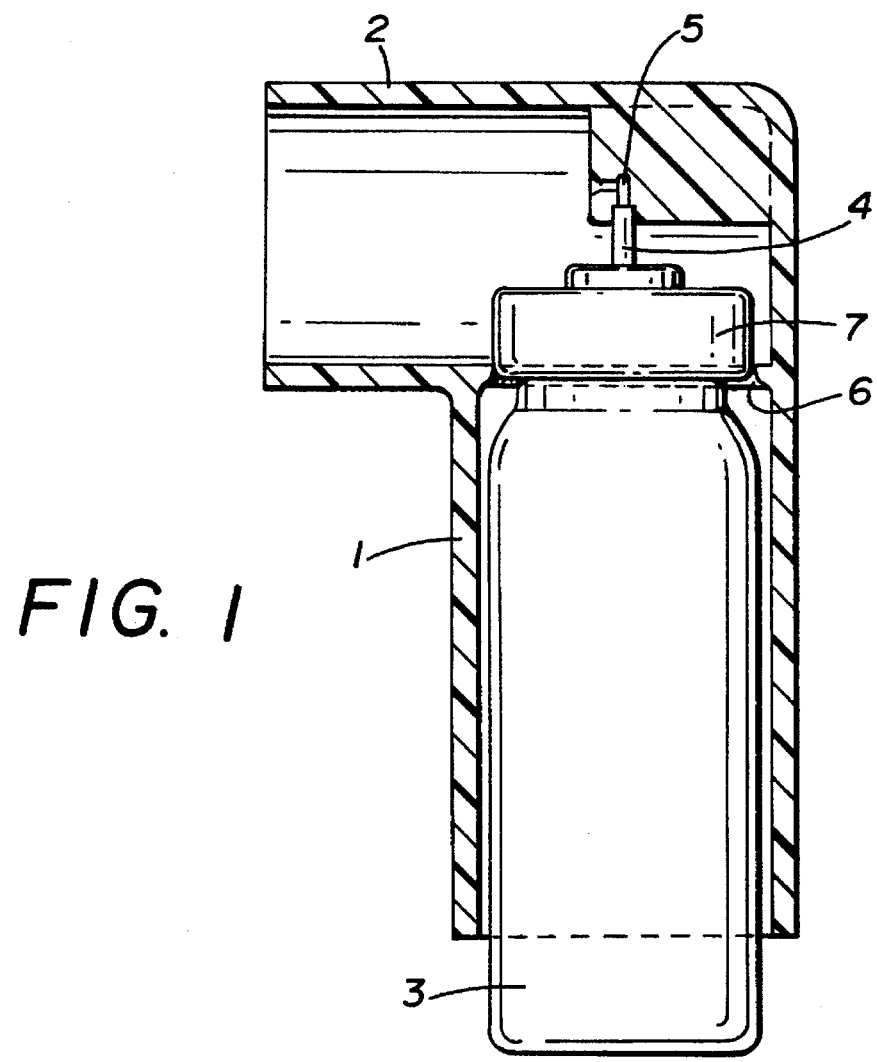
FIG. 1 shows the front view of device in neutral position, in its preferential form, in AA section.
Figure 2:
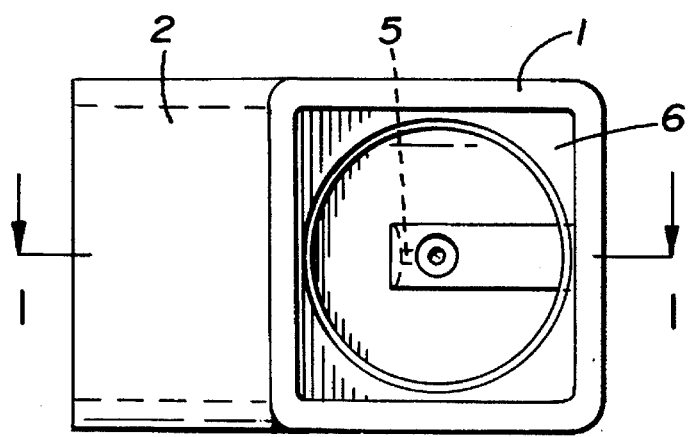
FIG. 2 shows underneath view, without regulating bottle.

In a preferential execution mode shown on FIGS. 1 and 2, the device conventionally consists of a body (1), equipped with a mouth piece (2), a regulating bottle (3), equipped with a rod for the release (4), which opens up into the injection duct (5) of the body, and the product is being released when user presses regulating bottle (3) onto the body (1), which manoeuver shall slide bottle into body.

The appliance that acts as a valve consists of the shouldering (6) of body fitted against the wall (7) of the regulating bottle (3). When using the appliance, user exhales deeply, and then brings the mouth piece (2) to his mouth and attempts to breathe into the appliance. Inhaling is greatly obstructed or even impossible due to the closing of air passage by the shouldering (6) extending inwardly of the body against the wall (7) of regulating bottle, and this gives the user all the time he needs to press on the regulating bottle (3) which allows him to inhale freely when the wall (7) of the regulating bottle goes beyond the shouldering of the body and triggers, in synchronization or slightly out of synchronization, the spraying of one dose of the product into the mouth piece (2) of the body.

Figure 3:
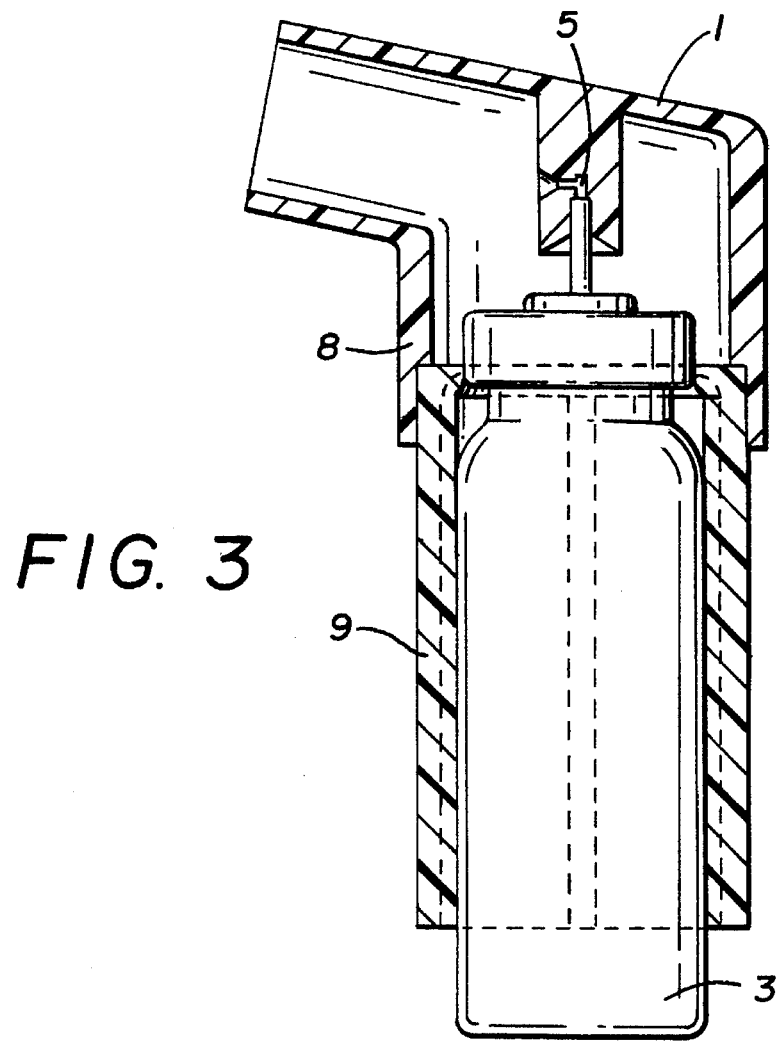
FIG. 3 shows front view of the first variation, still in neutral position, in AA section.
Figure 4:
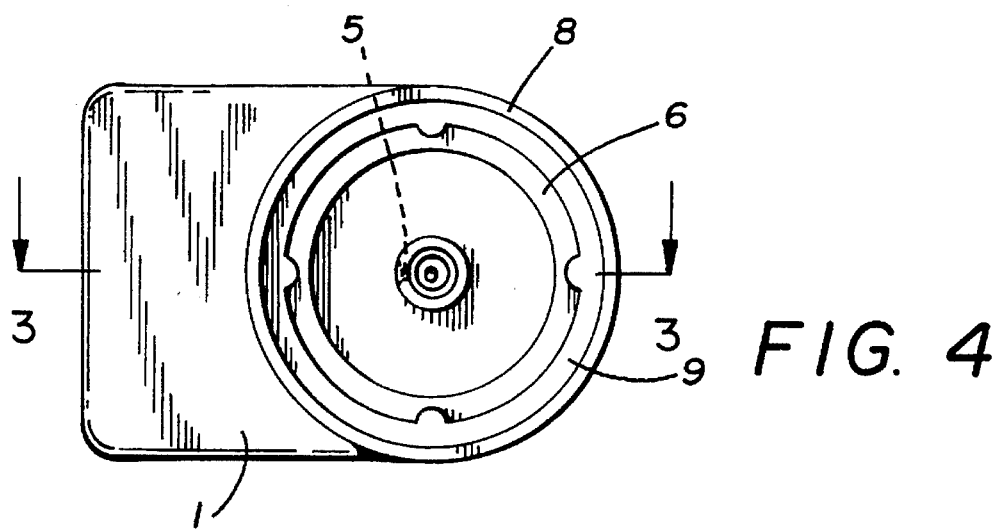
FIG. 4 shows underneath view, without regulating bottle.

In a first variation, as represented in FIGS. 3 and 4, the device has the same design and the same methods, but the body (1) is made of two parts, (8) and (9), firmly joined together, glued or welded, or attached by any other method. These two pieces are intended to facilitate the manufacturing of these pieces and to adapt them to various regulating bottles, since only piece (9) has to be modified, while the more complex piece (8) remains identical.

Figure 5:
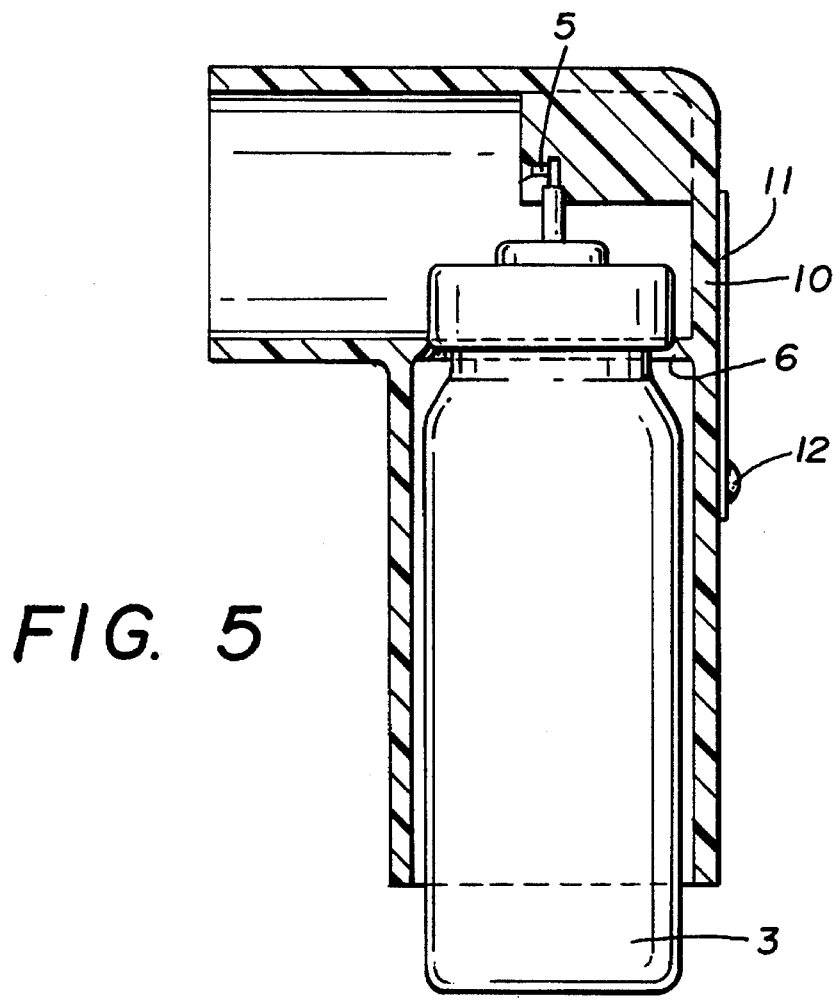
FIG. 5 shows front view of the second variation, in AA section.
Figure 6:
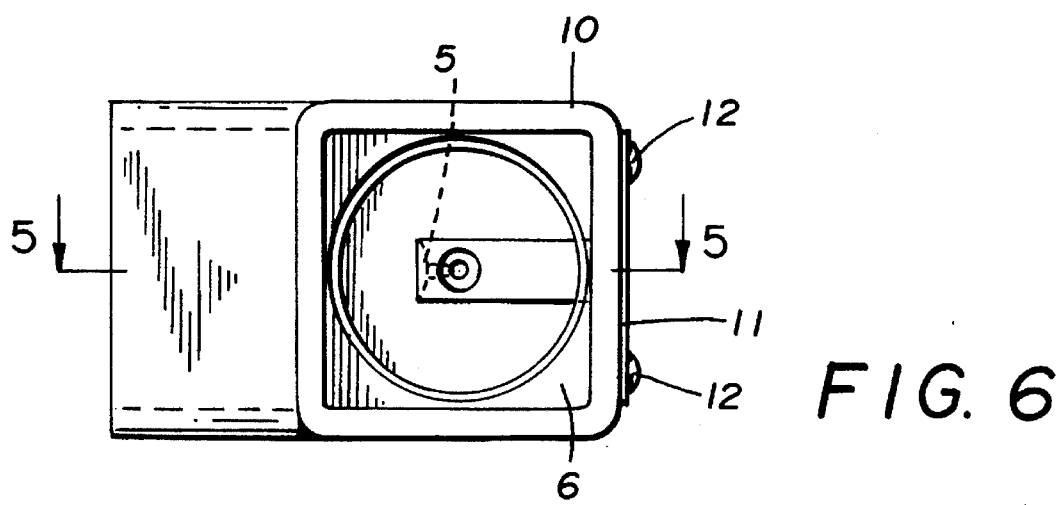
FIG. 6 shows underneath view, without regulating bottle.

In a second variation, represented in FIGS. 5 and 6, the device follows the design of the first variation, but, in addition thereto, it is equipped with a damper valve, consisting of two or more orifices (10) in the body and a thin sheet (11) attached to the body by hot riveting (12), or by any other method: gluing, fitting, and could even be molded. This thin sheet could be steel, be a synthetic material or any other flexible and elastic material. This valve allows user to first exhale while having the appliance in his mouth.

Figure 7:
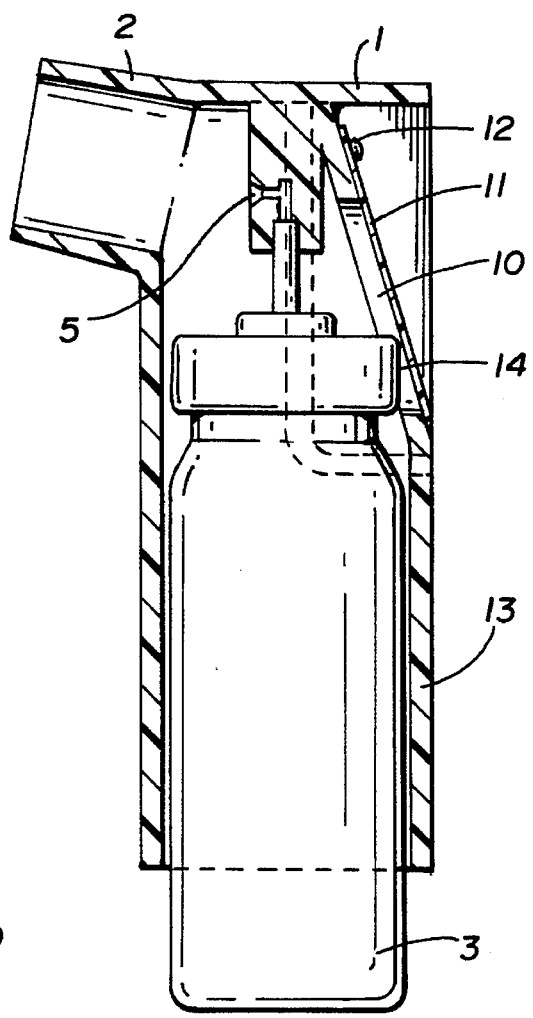
FIG. 7 shows front view of third variation in neutral position, in AA section.
Figure 8:
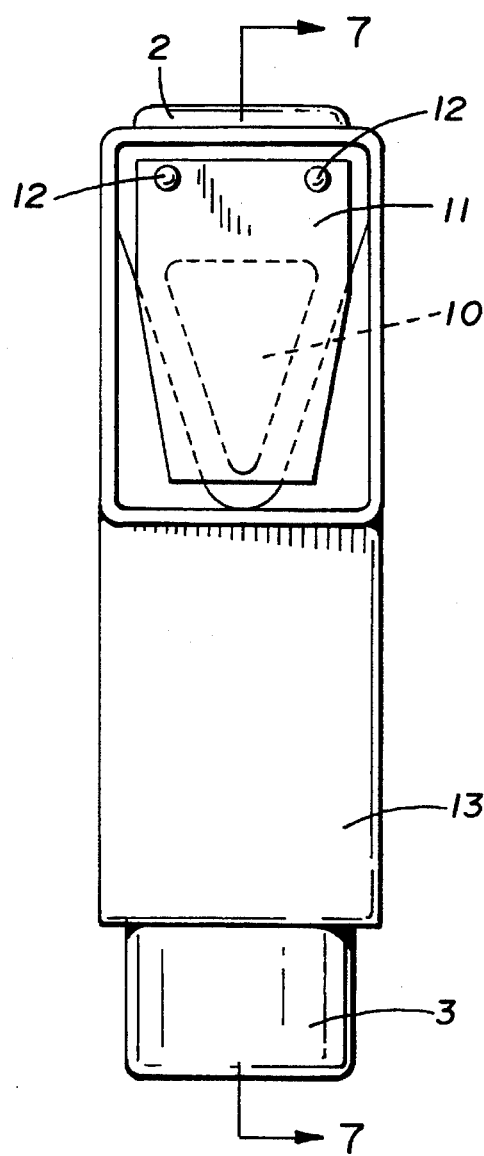
FIG. 8 shows right side view.

In a fourth variation of execution, shown in FIGS. 7 and 8, the device still equipped with a body (1), equipped with a mouth piece (2), an injection duct (5). This time, the receiving end of the bottle (13) of body (1) has a practical cylindrical shape and is fitted against regulating bottle (3) in order to be somewhat waterproof. The body is equipped with a damper valve consisting of one or more orifices (10) and the thin sheet (11) which allows the user to exhale through the appliance, this damper valve is also the valve of the device. Indeed, when the regulating bottle is activated, its generator (14) shall push the thin sheet (11) of the damper valve, thereby opening the latter, which allows patient to inhale simultaneously while releasing a dose of active element into the mouth piece. There also, the thin sheet (11) is attached with hot riveting or any other usual method.

Figure 9:
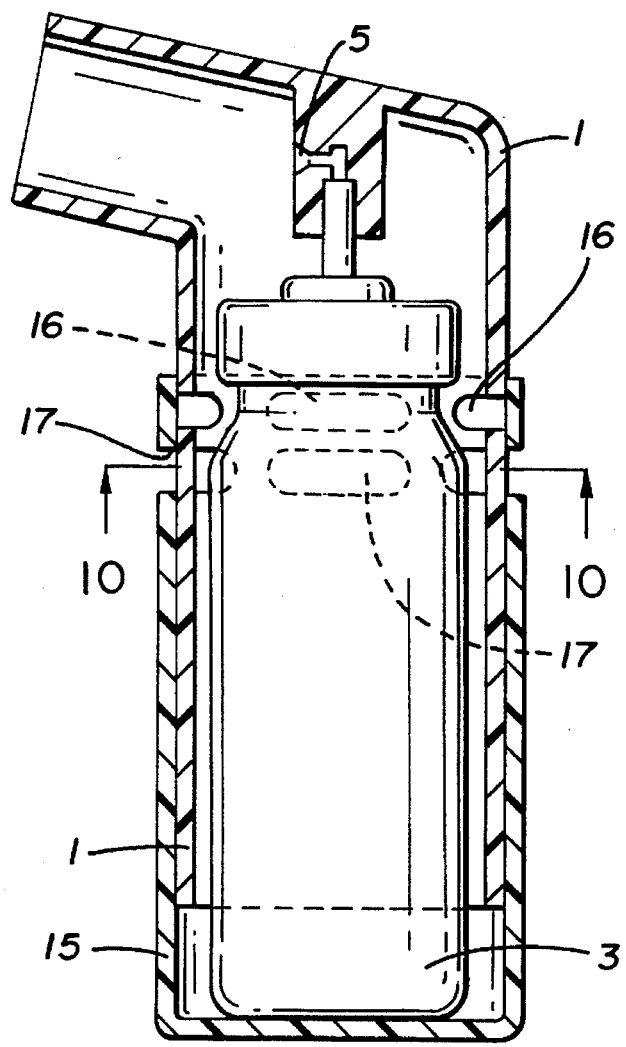
FIG. 9 shows front view of fourth variation in neutral position, in AA section.
Figure 10:
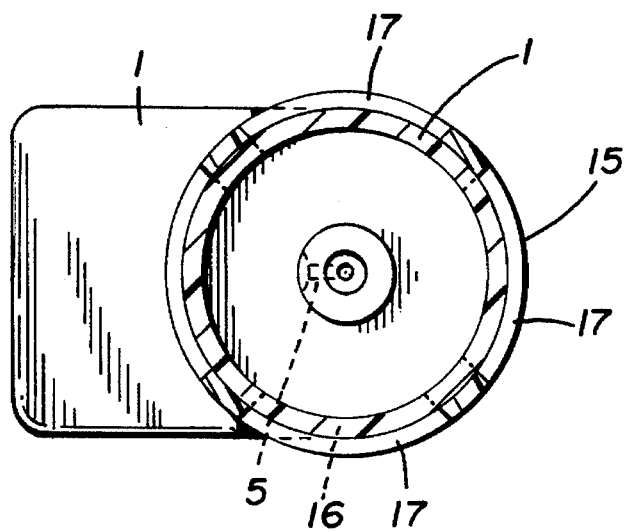
FIG. 10 shows underneath view, without regulating bottle, in BB section.

In a fifth variation of execution shown in FIGS. 9 and 10, the regulating bottle (3) is placed in a runner (15) which slides in a waterproof manner around the body (1) of the appliance. The valve of the appliance consists of the slots (16) of the body (1) and (17) of runner (15). These slots shall fit when user activates the regulating bottle via runner (15)

and they allow user to inhale, always in synchronization with the injecting of a dose of the product.

This execution gives an additional advantage, namely of being waterproof when the appliance is in neutral position and when the cap is placed over the mouth piece (not shown), thus protecting the appliance against dust contamination and other dirt which is frequently found in the pockets of clothing where the appliance is usually stored.

In this execution, it should be noted that the runner (15) is removable and allows for a conventional use of the appliance, where synchronization is offered as an option for the user.

Note: Whatever the execution method may be, it is possible in certain cases, to use regulating bottles that are different from the original bottles, by using spacers which shall compensate for the functional dimensional differences whenever possible.

The device in this invention may further be used in all cases of contamination of respiratory tracts by nuclear elements or other pollutants.

We claim:

1. An appliance intended to synchronize inhaling by the user through the appliance with spraying of a dose of active element released from a regulating bottle comprising:

(a) a closing means, acting as a valve, for restricting inhaling by the user through the appliance until the user executes a manoeuver which releases the dose of active element from the regulating bottle, which then provides for free inhalation, thereby ensuring a good flow of the dose into the respiratory system of the user;

(b) a damper valve to allow the user to exhale through the appliance prior to an attempt to inhale; and (c) said damper valve is positioned to be opened by the regulating bottle sliding into the appliance, and said closing means further includes said damper valve.

2. An appliance according to claim 1, further comprising a movable runner in which the regulating bottle can be placed, said runner activating the means to release of the regulating bottle.

3. An appliance according to claim 2, wherein said closing means includes at least one slot in a body portion of the appliance and at least one slot in said runner, said slots being fit together when the user activates the regulating bottle via said runner, thereby allowing the user to inhale.

4. An appliance according to claim 2, wherein said runner includes means to seal the appliance from dust contamination and other dirt.

5. In combination with a regulating bottle having a means to release a dose of active element therefrom, an appliance for synchronizing the inhalation of the dose of active element by a user through the appliance with the release of the dose of active element from the regulating bottle, the appliance comprising:

(a) a body for receiving the means to release the dose from the regulating bottle, said body having a mouth piece through which the dose of active element is received by the user;

(b) valve means within said body of the appliance for restricting the inhalation by the user through the appliance until the means to release the dose of active element from the regulating bottle is activated by the user;

(c) a movable runner in which the regulating bottle can be placed, said runner being movable with the regulating bottle to release the active element from the regulating bottle; and (d) said valve means includes at least one slot in said body of the appliance and at least one slot in said runner, said slots being fit together when the user activates the regulating bottle via said runner, thereby allowing the user to inhale.

6. The combination of claim 5, wherein said runner includes means to seal the appliance and regulating bottle from dust contamination and other dirt.

7. An appliance intended to synchronize inhaling by the user through the appliance with spraying of a dose of active element released from a regulating bottle comprising:

(a) a closing means, acting as a valve, for restricting inhaling by the user through the appliance until the user executes a manoeuver which releases the dose of active element from the regulating bottle, which then provides for free inhalation, thereby ensuring a good flow of the dose into the respiratory system of the user;

(b) a movable runner in which the regulating bottle can be placed, said runner being movable with the regulating bottle to release the active element from the regulating bottle; and (c) said closing means includes at least one slot in a body portion of the appliance and at least one slot in said runner, said slots being fit together when the user activates the regulating bottle via said runner, thereby allowing the user to inhale.

8. An appliance according to claim 7, wherein said runner includes means to seal the appliance from dust contamination and other dirt.

* * * * *